United States Patent [19]
Suzuki et al.

[11] Patent Number: 5,947,898
[45] Date of Patent: Sep. 7, 1999

[54] NON-CONTACT TYPE TONOMETER

[75] Inventors: Nobuo Suzuki, Nukata-gun; Munehiro Nakao, Toyokawa; Tetsuyuki Miwa, Nukata-gun, all of Japan

[73] Assignee: Nidek Co., Ltd., Gamagori, Japan

[21] Appl. No.: 08/864,622

[22] Filed: May 28, 1997

[30]       Foreign Application Priority Data

May 31, 1996   [JP]   Japan ................................. 8-161074

[51] Int. Cl.⁶ ....................................................... A61B 3/16
[52] U.S. Cl. ............................................................. 600/405
[58] Field of Search ................................... 600/398–406

[56]             References Cited

U.S. PATENT DOCUMENTS

| | | |
|---|---|---|
| 4,770,181 | 9/1988 | Tomoda . |
| 4,947,849 | 8/1990 | Takahashi et al. . |
| 5,002,056 | 3/1991 | Takahashi et al. . |
| 5,048,526 | 9/1991 | Tomoda . |
| 5,165,408 | 11/1992 | Tomoda . |
| 5,279,300 | 1/1994 | Miwa et al. . |
| 5,634,463 | 6/1997 | Hayafuji ................................. 600/398 |
| 5,779,633 | 7/1998 | Luce ........................................ 600/398 |

FOREIGN PATENT DOCUMENTS

| | | |
|---|---|---|
| A 63-283621 | 11/1988 | Japan . |
| A 2-104331 | 4/1990 | Japan . |
| A 3-118034 | 5/1991 | Japan . |
| A 6-7305 | 1/1994 | Japan . |
| A 7-16208 | 1/1995 | Japan . |
| A 7-16212 | 1/1995 | Japan . |
| A 7-100116 | 4/1995 | Japan . |

*Primary Examiner*—Samuel Gilbert
*Attorney, Agent, or Firm*—Oliff & Berridge, PLC

[57]               ABSTRACT

In a non-contact type tonometer for blowing compressed gas against an examined eye through a nozzle, when a piston returns to an initial position by a biasing unit for biasing so as to return the piston to the initial position, a piston driving unit is actuated so as to attenuate the piston return speed by applying a force in the upwardly moving direction. Further, the piston is attached a piston rod so as to move in the axial direction of a cylinder, and is provided a gas passage which is closed when the gas is compressed and is opened when the piston returns to the initial position by the movement of the piston rod. Thus, the air compression chamber within the cylinder is caused to conductively connect to the atmospheric open chamber to thereby restrain the interior of the cylinder from becoming negative in pressure. In this way, it is possible to suppress the sucking-in of tears, dust, eyelashes and the like through the nozzle as effectively as possible with a simple structure.

14 Claims, 4 Drawing Sheets

5,947,898

NON-CONTACT TYPE TONOMETER

BACKGROUND OF THE INVENTION

1. Field of the Invention

The present invention relates to a non-contact type tonometer for measuring intraocular pressure by compressing fluid in a cylinder, blowing compressed fluid against an examined eye, and detecting a deformed state in the cornea of the examined eye.

2. Description of the Related Art

As a non-contact type tonometer, there is known one of a mechanism in which air in a cylinder is compressed by a piston and compressed air is blown against an examined eye through a nozzle from a compression chamber for conductively connecting to the cylinder to deform the cornea. For the intraocular pressure of the examined eye, a deformed state in the cornea caused by blowing compressed air is detected, and air pressure when the cornea has been deformed into a predetermined state is directly or indirectly detected to thereby measure on the basis of the air pressure thus detected at that time. The air to be blown against the examined eye is compressed by supplying current to a driving device such as a solenoid to drive the piston. After the detection of the deformed state of the cornea, energizing of the piston driving device is stopped to return the piston to the initial position by a restoring force such as a spring. At this time, air is sucked in through the nozzle.

In a process of sucking in outside air through the nozzle by such return of the piston, however, when the piston is suddenly returned, tears, dust, eyelashes and the like are prone to be sucked in the cylinder through the nozzle. The tears, dust, eyelashes and the like thus sucked contaminate the optical system arranged behind the nozzle, and eyelashes and the like may enter a gap between cylinder and piston to lock the piston. Further, since the dust and the like which have been sucked are blown against the examined eye again, it is not desirable also in view of hygiene.

In the light of the above-described problems, it is a technical problem of the present invention to provide a non-contact type tonometer capable of restraining tears, dust, eyelashes and the like from being sucked in through the nozzle as effectively as possible with a simple structure.

SUMMARY OF THE INVENTION

In order to solve the above-described problems, the present invention is characterized by having the following structures.

(1) The present invention is characterized in that in a non-contact type tonometer for blowing compressed gas against an examined eye through a nozzle, there are provided gas compression means for compressing gas by moving a piston from an initial position within a gas chamber by driving means; biasing means for biasing so as to return the piston to the initial position; pressure detection means for directly or indirectly detecting a pressure of the gas; deformation detection means for detecting a corneal deformed state caused by blowing the compressed gas; intraocular pressure calculation means for calculating an intraocular pressure on the basis of a detection result by the deformation detection means and the pressure detection means; and control means for actuating the driving means so as to attenuate, when the piston returns to the initial position by the biasing means, its return speed. In this way, it is possible to suppress the sucking-in of tears, dust, eyelashes and the like through the nozzle as effectively as possible with a simple structure.

DETAILED DESCRIPTION OF PREFERRED EMBODIMENT

Figure 1:
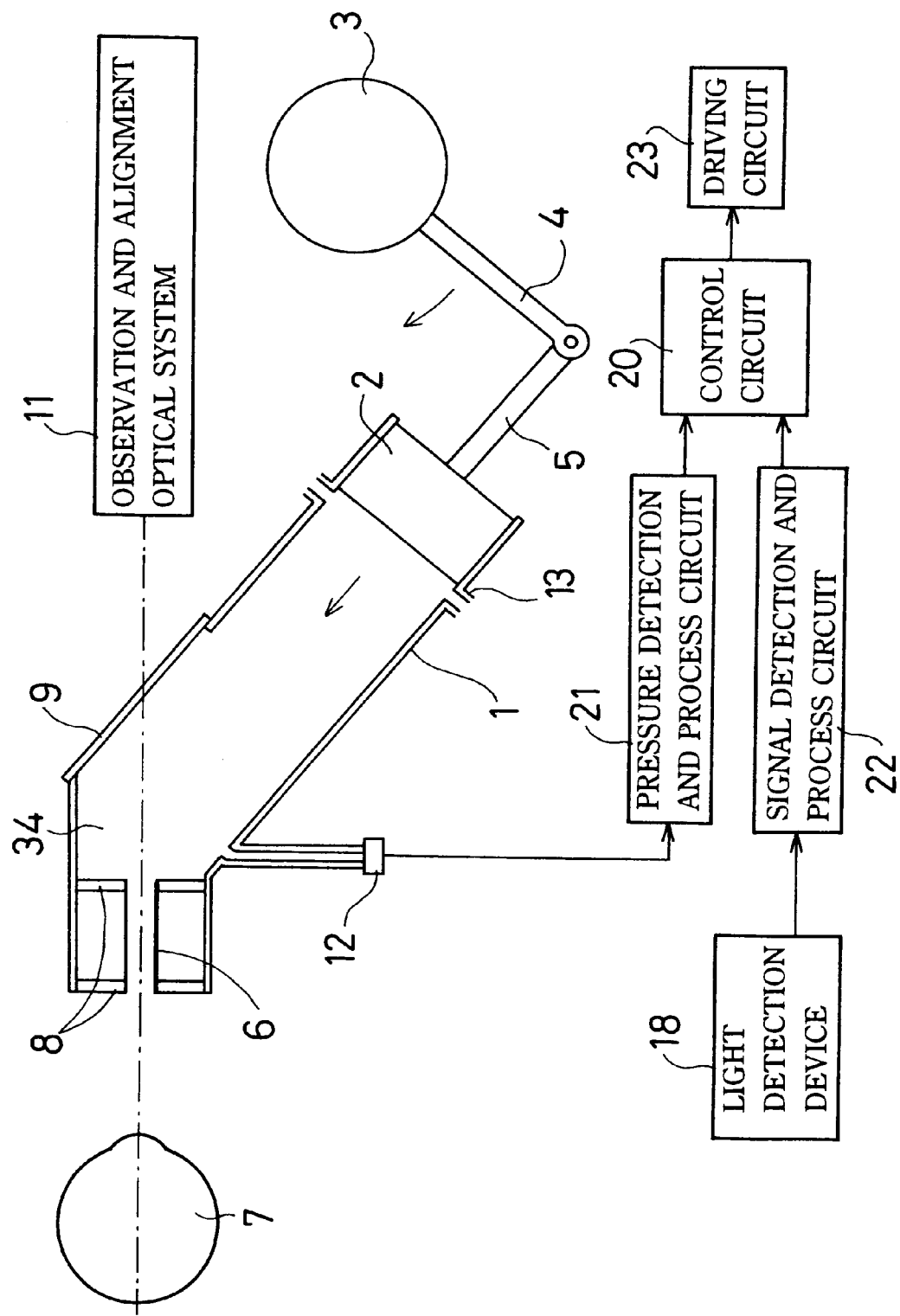
FIG. 1 is a view showing the outline side structure and control system of an air compression mechanism for a non-contact type tonometer according to an embodiment.
Figure 2:
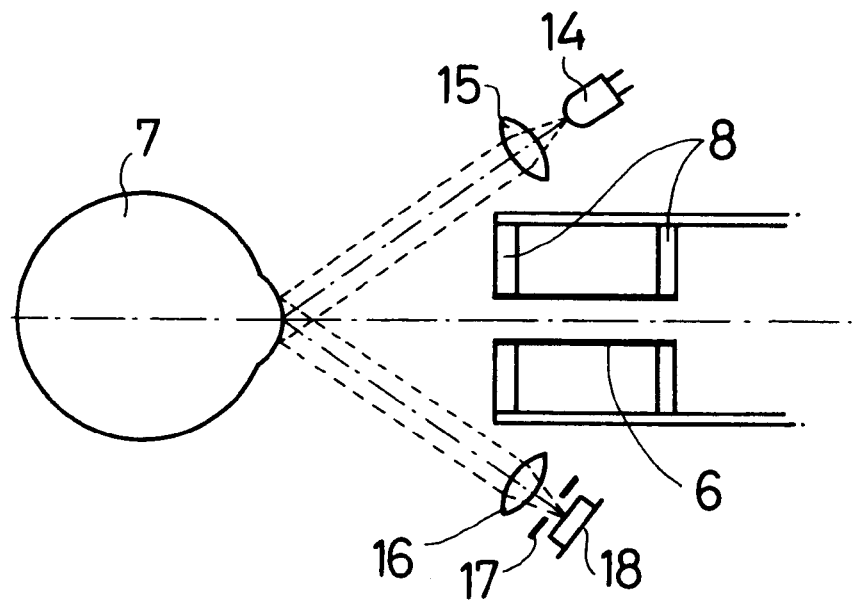
FIG. 2 is a view, as viewed from above, showing the optical system near the nozzle of an air compression mechanism for a non-contact type tonometer according to an embodiment.

Hereinafter, the description will be made of the present embodiment with reference to the drawings. FIG. 1 is a view showing the outline side structure and control system of an air compression mechanism for generating fluid pressure for a non-contact type tonometer according to an embodiment. FIG. 2 is a view showing the optical system near the nozzle as viewed from above.

In FIGS. 1 and 2, reference numeral 1 designates a cylinder portion for air compression, which is provided inclined to the horizontal line of the tonometer body; 2, a piston; and 3, a rotary solenoid, which presses the piston 2 upwardly through an arm 4 and a connecting rod (piston rod) 5 when driving current is supplied. Air, which has been compressed by the rise of the piston 2 in an air compression chamber 34 which conductively connects to the cylinder portion 1, is blown against the cornea of the examined eye 7 through a nozzle 6. The rotary solenoid 3 is provided with a coiled spring 3A, and when the supplied current is cut off or reduced, the biasing force of the coiled spring in the lowering direction causes the raised piston 2 to lower to the initial position.

Reference numeral 8 designates a transparent glass plate, which holds the nozzle 6 and transmits observation light or alignment light. The glass plate 8 also constitutes a side wall of the air compression chamber 34. A transparent glass plate 9 is provided behind the nozzle 6, and constitutes the rear wall of the air compression chamber 34, transmitting observation light or alignment light. Behind the glass plate 9, there is arranged an observation and alignment optical system 11, which, however, is hardly related to the present invention and therefore the description thereof will be omitted.

Reference numeral 12 designates a pressure sensor for detecting the pressure in the air compression chamber 34; and 13, an air vent hole, which reduces the resistance until the initial speed is given to the piston 2, and provides change in pressure of rise which is proportionate to time.

Reference numeral 14 designates infrared LED (See FIG. 2) for detection of the corneal pressure-flattened state. A light emitted from LED 14 is made into parallel luminous flux by a collimator lens 15, and is projected to the cornea of the examined eye. The light reflected by the cornea passes through a light-receiving lens 16 and a pin-hole plate 17 and is received by a light detection device 18. The optical system for detection of a corneal pressure-flattened state is arranged so that the quantity of light received by the light detection device 18 becomes the maximum when the examined eye is in a predetermined pressure-flattened state.

Reference numeral 20 designates a control circuit; 21, a pressure detection and process circuit for processing a signal from the pressure sensor 12; 22, a signal detection and process circuit for processing a signal from the light detection device 18; and 23, a driving circuit for driving the rotary solenoid 3.

The operation of a non-contact type tonometer having the above-described structure will be described hereinafter.

An examiner places the examined eye 7 at a predetermined position, and handles a joy stick (not shown) to perform alignment adjustment. After the completion of the alignment, the examiner presses a measurement starting switch (or the control circuit 20 automatically sends a measurement starting signal in accordance with a signal from the alignment optical system) to start measurement. On receipt of the measurement starting signal, the control circuit 20 supplies current (voltage) as driving energy capable of actuating the rotary solenoid 3 thereto through the driving circuit 23 to drive it.

In this respect, the rotary solenoid 3 in a tonometer according to the embodiment has been set when the power supply for this device is turned on, so that weak current of such a degree that it does not operate (the piston at the initial position does not operate) against the biasing force of the coiled spring flows (a low voltage is applied). Generally, the rotary solenoid has a slight gap between an electromagnetic plane and a ball supporting the coiled spring, and when current capable of starting an operation is supplied in a state in which no current has been supplied, the electromagnetic plane strikes the ball to cause metallic sound on driving the rotary solenoid. When this metallic sound is caused during measurement, it may surprise the examinee. Accordingly, it is possible to cause the electromagnetic plane and the ball to be in a contact state by causing such weak current to flow through the rotary solenoid 3 as not to actuate it at all times, thus causing no metallic sound at the input of a measurement starting signal. Thereby, it is possible to reduce the operating sound of the rotary solenoid 3.

Further current through the rotary solenoid 3 raises the piston 2. The rise of the piston 2 compresses the air in the air compression chamber 34 to blow the compressed air toward the cornea of the examined eye 7 through the nozzle 6. The cornea of the examined eye 7 is gradually deformed by the compressed air thus blown. The reflected light, by the cornea, of light projected from the LED 14 is received by the light detection device 18 to detect the deformed state of the cornea by means of the light detection device 18.

When the signal detection and process circuit 22 detects through a signal from the light detection device 18 that the quantity of the received light reaches a predetermined peak, that is, when it is detected that a predetermined pressure-flattened state has been attained, the control circuit 20 obtains the intraocular pressure on the basis of this detection signal. A tonometer according to the present embodiment calculates the intraocular pressure by indirectly obtaining the air pressure on the basis of time required until the quantity of the received light reaches the maximum value since the commencement of the measurement. For the details of the measurement of intraocular pressure, refer to "Ophthalmic Apparatus" disclosed in Japanese Published Unexamined Patent Application No. Hei 4-297226 by the present applicant.

Also, when it is detected that the examined eye has entered a predetermined pressure-flattened state, or when a lapse of predetermined time from the commencement of measurement is detected by time supervision (or when a predetermined pressure is obtained), the control circuit 20 stops the supply of current to the rotary solenoid 3. Although the piston 2 rises by an inertia force even after the supply of current to the rotary solenoid 3 is stopped, a biasing force caused by the coiled spring in the lowering direction is exerted on the piston 2. The biasing force of the coiled spring and the gravity applied to the piston 2 attenuate the speed of the piston 2 to stop it once, and thereafter to lower.

When the piston 2 lowers and the air compression chamber 34 reaches negative pressure, air is sucked in through the nozzle. Thus, the biasing force of the coiled spring and the gravity applied to the piston 2 increase the speed of the piston 2 for lowering, and therefore, air is suddenly sucked in through the nozzle. In the tonometer according to the present embodiment, by supplying weak current thereafter instead of cutting off the supply current to the rotary solenoid 3 during lowering of the piston 2, the lowering speed thereof is attenuated to suppress the sudden sucking of air through the nozzle. In this respect, the piston lowering speed can be attenuated even by supplying weak current to the rotary solenoid 3 without cutting off the supply current once, but in this case, inertia force promotes the rise of the piston 2, possibly blowing extra air against the examined eye, and therefore, it is preferable to cut off once as in the embodiment.

The amount of supplied weak current at this time will be described.

Figure 3:
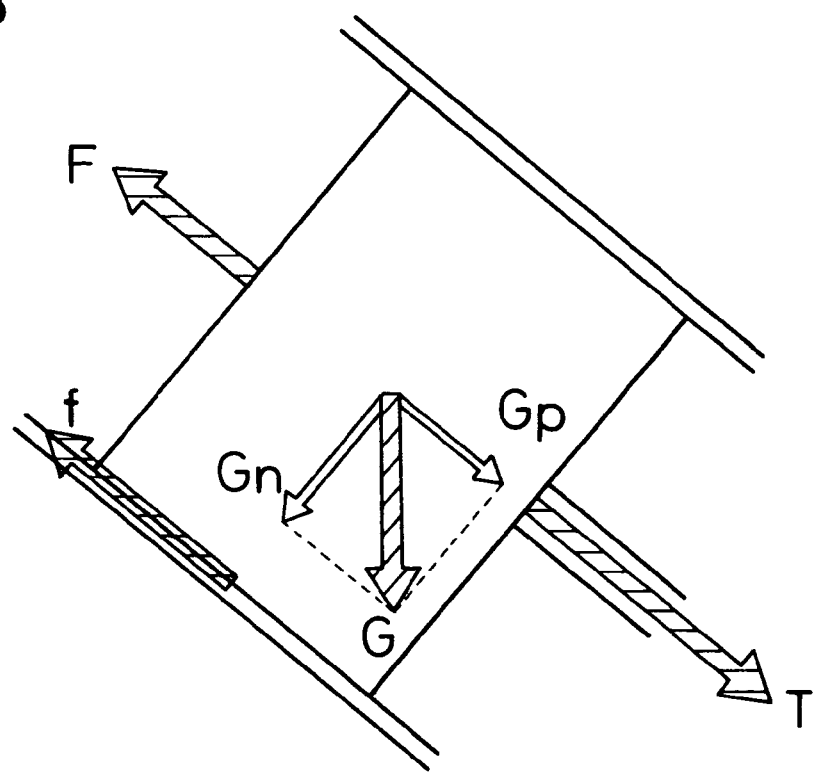
FIG. 3 is an explanatory view for showing balance of a force applied to the piston during lowering.

The balance of a force applied to the piston 2 during lowering will be described with reference to FIG. 3. As a force to lower the piston 2, the gravity G of the piston 2 and the biasing force T caused by the spring are exerted. Since the cylinder portion 1 is inclined to the horizontal line, the gravity G can be divided into two component forces: Gp along the wall surface, and Gn perpendicular to the wall surface. In this respect, in the present embodiment, the coiled spring provided within the rotary solenoid 3 is used and therefore, movement of the piston 2 is sufficiently small as compared with the length of the coiled spring. To this end, the biasing force T caused by the spring can be considered to be substantially constant irrespective of the position of the piston.

As a force of the piston 2 in the upper direction during lowering, a frictional force f and a force F caused by supplying weak current to the rotary solenoid 3 to drive it are exerted. The frictional force f is proportionate to the magnitude of Gn which becomes a vertical drag while the force F due to the supply of the current varies with the magnitude of the current supplied to the rotary solenoid 3.

The component forces Gp and Gn of the gravity G and the frictional force f are dependent on the inclination angle of the cylinder portion 1, and are substantially constant, and the biasing force T due to the spring is also substantially constant, and therefore, the lowering speed can be controlled by controlling the force F due to the solenoid. Accordingly, such weak current as to cause the resultant force of these four forces to somewhat decline is supplied to the rotary solenoid 3 during lowering of the piston 2 whereby it is possible to suppress the sucking-in through the nozzle 6 by making the lowering speed slower. The quantity of current supplied to the rotary solenoid 3 is experimentally determined so that the piston does not operate against the biasing force of the coiled spring when it is positioned at the initial position.

Next, timing for supplying weak current will be described.

After the current is cut off, the gravity and the biasing force caused by the coiled spring are exerted on the piston 2 to gradually negate the inertia force. Thereafter, the piston 2 diverts to lowering. Interlocked with the movement of the piston 2, the pressure value of the air compression chamber 34 also shows the maximum value, thereafter decreases, and the pressure becomes negative because of the lowered piston 2. When the pressure in the air compression chamber 34 becomes negative, air is sucked in through the nozzle. Therefore, and weak current is supplied so as to drive the rotary solenoid 3 before the lowering acceleration is increased.

For a rotary solenoid which is driving means for a piston, and the like, there is generally a time lag of several minutes until it starts to effectively drive after the supply of current is started. Accordingly, it is necessary to actually determine timing for supplying weak current to the rotary solenoid 3 in consideration of this time lag. When the timing for supplying weak current is too late, the pressure within the air compression chamber 34 becomes negative, and the ascending force is applied after the lowering speed of the piston 2 is increased, thus reducing the deceleration effect. When the timing is too early to the contrary and the rotary solenoid 3 is driven while the piston 2 is rising, the rise of the piston 2 is promoted by the inertia force, leading to blowing extra air to the examined eye.

Figure 4:
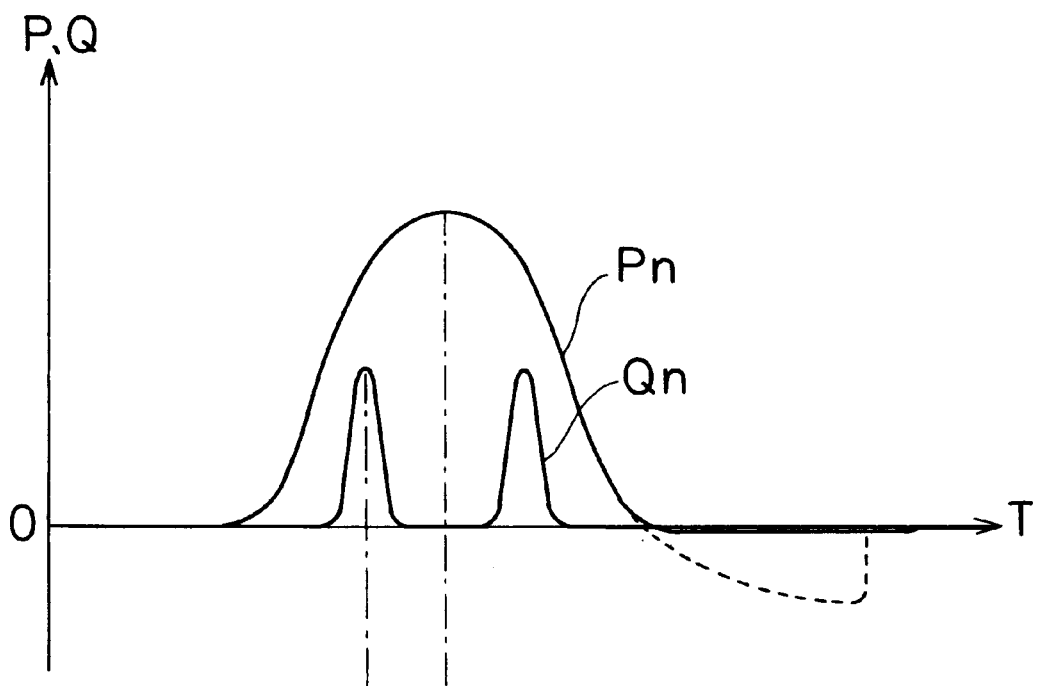
FIGS. 4a and 4b is a time series diagram showing changes in pressure within the cylinder during piston driving, a quantity of received light in a light detection device for detecting a pressure-flattened state, and supplied voltage to the piston driving device.
Figure 4:
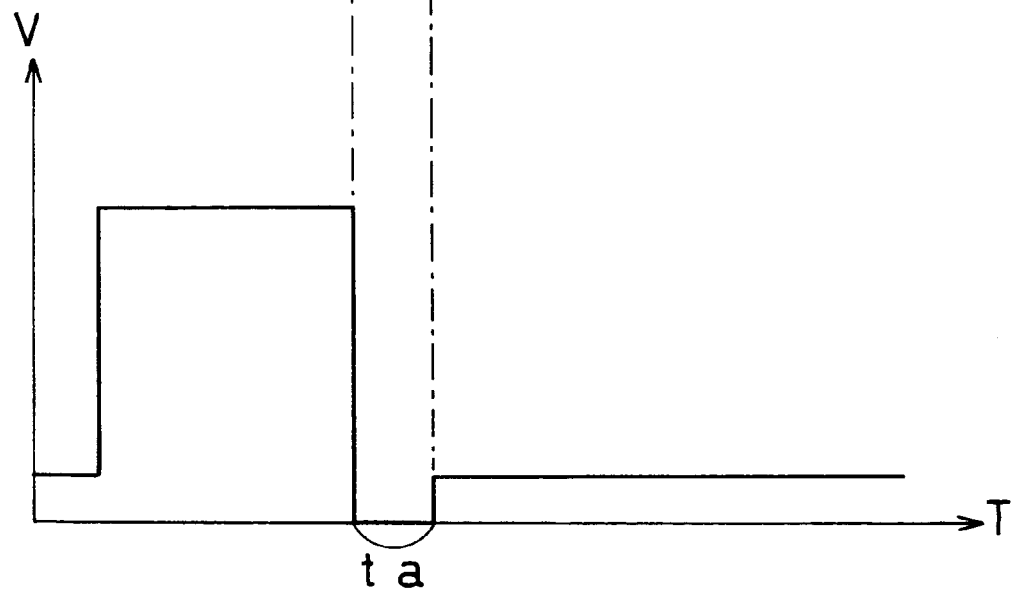

FIG. 4A is a view showing changes, in time series, in detected pressure Pn by the pressure sensor 12 and quantity of received light Qn in the light detection device 18, and FIG. 4B is a view showing changes in voltage V for supplying current to the rotary solenoid 3 in time series. According to the experiment by the present inventor, when the supply of weak current is started by applying voltage near a place where the pressure value measured by the pressure sensor 12 reaches the peak as shown in FIG. 4, the degree at which the pressure value becomes negative could be suppressed low most effectively without blowing extra air against the examined eye (the dotted line for detected pressure Pn in FIG. 4A shows conventional change in pressure). Thus, in the tonometer according to the present embodiment, for example, time ta during which the pressure value indicates the peak after the supply of voltage (current) is cut off is obtained experimentally, and this time ta is stored in a memory circuit within the control circuit 20 in advance. During measurement, low voltage is applied to supply weak current at timing that the predetermined time ta has elapsed after the supply of voltage (current) is cut off.

In this respect, as timing for starting the supply of weak current (low voltage) to the rotary solenoid 3, it may be possible to supply at timing that the time when the pressure value obtained each time measurement is made reaches the peak is detected instead of supplying after a lapse of the predetermined time after the voltage (current) is cut off. In this case, since driving current is supplied to the rotary solenoid 3 after the pressure value reaches the peak, air at high pressure need not be blown against the examined eye even if there are some individual differences in response of the rotary solenoid 3.

Further, as the timing for supplying weak current to the rotary solenoid 3, it may be possible to detect the moving speed, position and the like of the piston 2 by a sensor to perform on the basis of this detection result instead of performing on the basis of a pressure signal. For example, a rotary encoder is mounted to the rotary shaft of the rotary solenoid 3 to detect the movement of the piston 2 on the basis of the movement of the rotary shaft.

Figure 5:
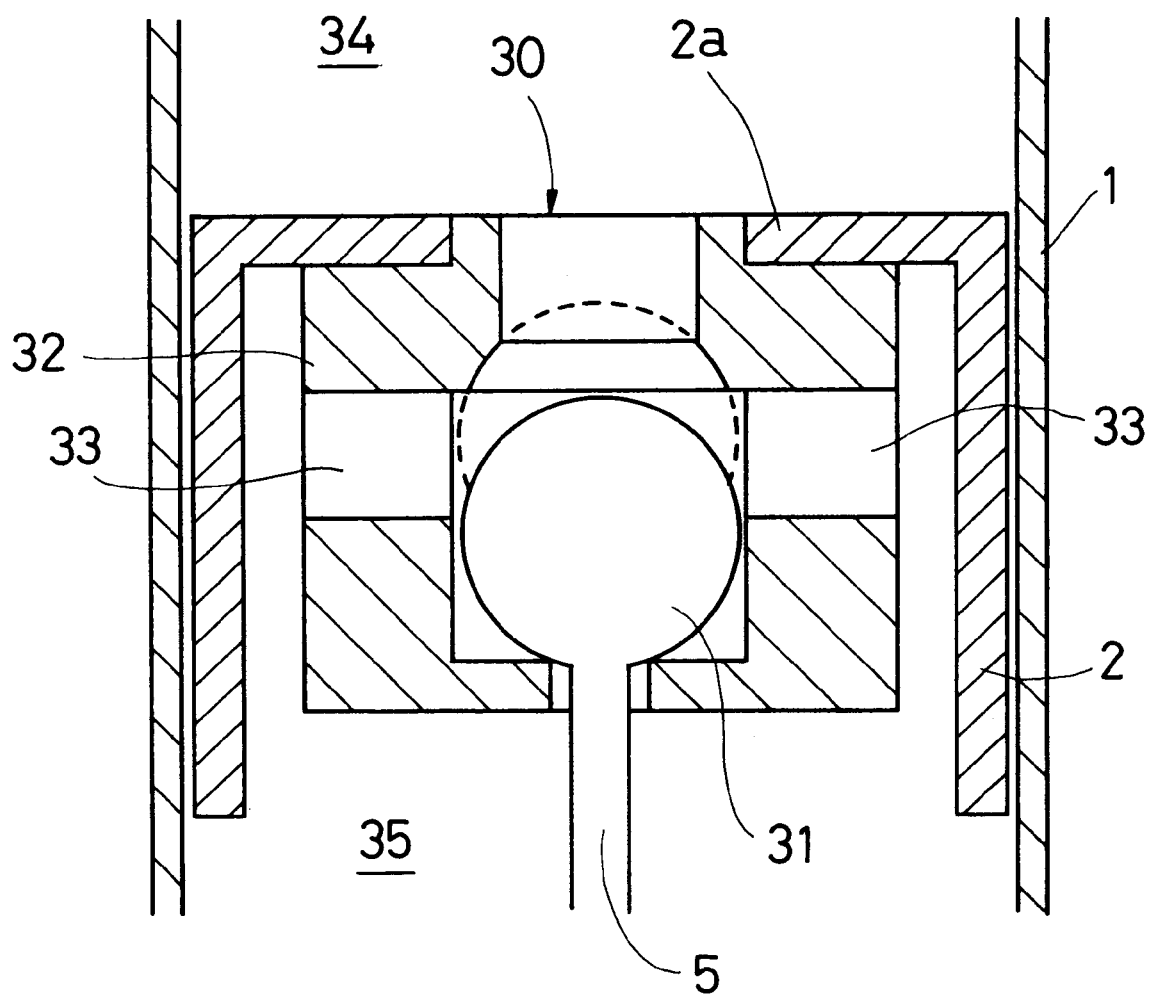
FIG. 5 is a cross-sectional view showing the piston equipped with a valve mechanism.

As described above, the tonometer according to the present embodiment is capable of suppressing the sudden sucking-in of air through the nozzle by making the lowering speed of the piston 2 slower, but further when such a valve mechanism as shown in FIG. 5 is provided for the piston 2, it is possible to suppress the sucking-in of air through the nozzle more effectively.

Referring to FIG. 5, a driving valve 31 having a substantially spherical plane is formed at the upper end of a connecting rod 5, and the driving valve 31 is so held in a cylindrical valve driving chamber portion 32 fixed to the lower side of the upper wall 2a of the piston 2 as to vertically move freely. The driving chamber portion 32 is, at the upper portion, formed into such a shape as to fit to the substantially spherical plane of the driving valve 31, and a through hole 30 for connecting to the air compression chamber 34 is provided at the central portion thereof. Also, the valve driving chamber portion 32 is, on the side walls, provided with transverse holes 33, through which an atmospheric open chamber 35 below the piston 2 conductively connects to the air compression chamber 34 when the driving valve 31 lowers. In this respect, the driving chamber portion 32 is preferably made of resin or the like in order to suppress the operation sound due to abutting during movement of the driving valve 31, occurrence of dust due to movement of the driving valve 31, and the like.

With the structure of the above-described valve, when the rotary solenoid 3 is driven to raise the connecting rod 5, the driving valve 31 raises the piston 2 while blocking the through hole 30 with the substantially spherical plane. The raised piston 2 compresses the air within the air compression chamber 34 to blow the compressed air against the cornea of the examined eye.

On the other hand, when the supply of current to the rotary solenoid 3 is cut off or weak current is supplied, the connecting rod 5 lowers and the driving valve 31 presses the piston 2 down while abutting against the bottom portion of the driving chamber portion 32. When the driving valve 31 lowers, the through hole 30 at the upper portion of the driving chamber portion 32 is released so that the atmospheric open chamber 35 comes to conductively connect to the air compression chamber 34 through the traverse holes 33, and the air in the atmospheric chamber 35 flows into the air compression chamber 34. Thereby, the sucking-in of tears, dust, eyelashes and the like can be suppressed by further reducing the flow-in of air through the nozzle 6.

The valve mechanism as described above is particularly convenient for a device in which the negative-pressure state is kept lower by making the piston lowering speed (return speed) slower as described above because the valve is opened interlocked with the movement of the piston irrespective of the negative pressure state in the air compression chamber 34.

As described above, according to the present invention, it is possible to suppress the sucking-in of tears, dust, eyelashes and the like through the nozzle without necessitating any complicated control.

Further, the provision of a valve which can be opened or closed without depending upon the difference in pressure enables the amount of air sucked in through the nozzle to be reduced.

What is claimed is:

1. A non-contact type tonometer for blowing compressed gas against an examined eye through a nozzle, comprising:
   driving means for driving a piston within a gas chamber,
   gas compression means for compressing gas by moving said piston from an initial position within said gas chamber by said driving means;

returning means for returning said piston to the initial position;

pressure detection means for directly or indirectly detecting a pressure of said gas;

determining means for determining a moment of maximum pressure on the basis of a detection result by said pressure detection means;

deformation detection means for detecting a corneal deformed state caused by blowing said compressed gas;

intraocular pressure calculation means for calculating an intraocular pressure on the basis of detection results by said deformation detection means and said pressure detection means; and supplying means for supplying driving energy to said driving means, wherein said driving energy includes:

first driving energy, of which a degree is weak such that said piston does not move from the initial position, supplied when power supply for the tonometer is turned on;

second driving energy, which is larger than a force of returning said piston to the initial position, supplied in response to a measurement starting signal so as to move said piston from the initial position; and third driving energy, which is smaller than the force of returning said piston to the initial position, supplied after obtaining the maximum pressure by said determining means so as to restrict return speed of said piston.

2. A non-contact type tonometer as defined in claim 1, wherein said pressure detection means directly detects the pressure by a pressure detection element, or has timing means for measuring a driving time of said driving means and indirectly detects said pressure on the basis of measured driving time.

3. A non-contact type tonometer as defined in claim 1, wherein said supplying means supplies a predetermined quantity of said third driving energy to said driving means when said piston returns to the initial position by said returning means, and wherein the predetermined quantity of said third driving energy is determined such that resultant force of gravity of said piston, frictional force between said piston and said gas chamber, returning force caused by said returning means and driving force caused by supplying said third driving energy to said driving means is declined.

4. A non-contact type tonometer as defined in claim 1, wherein said supplying means supplies said third driving energy to said driving means after the moment of the maximum pressure determined by said determining means.

5. A non-contact type tonometer as defined in claim 1, wherein said driving energy is driving current.

6. A non-contact type tonometer as defined in claim 1, wherein said driving means comprises a rotary solenoid.

7. A non-contact type tonometer as defined in claim 1, wherein said driving means comprises a rotary solenoid, and said returning means comprises a coiled spring arranged in said rotary solenoid.

8. A non-contact type tonometer as defined in claim 1, further comprising storage means for storing time which is from a moment when the supply of said second driving energy is stopped until the moment of the maximum pressure determined by said determining means.

9. A non-contact type tonometer as defined in claim 1, further comprising storage means for storing time which is from a moment when the supply of said second driving energy is started until the moment of the maximum pressure determined by said determining means.

10. A non-contact type tonometer as defined in claim 1, wherein said supplying means supplies a predetermined quantity of said first driving energy to said driving means when the power supply for the tonometer is turned on, and wherein the predetermined quantity of said first driving energy is determined such that resultant force of frictional force between said piston and said gas chamber and driving force caused by supplying said first driving energy to said driving means is substantially equal to resultant force of gravity of said piston and returning force caused by said returning means.

11. A non-contact type tonometer for blowing compressed gas against an examined eye through a nozzle, comprising:

driving means for driving a piston within a gas chamber, gas compression means for compressing gas by moving said piston from an initial position within said gas chamber by said driving means;

returning means for returning said piston to the initial piston;

pressure detection means for directly or indirectly detecting a pressure of said gas;

deformation detection means for detecting a corneal deformed state caused by blowing said compressed gas;

intraocular pressure calculation means for calculating an intraocular pressure on the basis of detection results by said deformation detection means and pressure detection means, and supplying means for supplying driving energy to said driving means, wherein said piston is provided with a gas passage which is closed when gas is compressed and is opened when said piston returns to the initial position.

12. A non-contact type tonometer as defined in claim 7, wherein said driving means includes a rotary solenoid.

13. A non-contact type tonometer as defined in claim 7, wherein said piston is attached a piston rod so as to move in an axial direction of said gas chamber, and said gas passage is closed when said gas is compressed and is opened when said piston returns to the initial position by movement of said piston rod.

14. A non-contact type tonometer as defined in claim 7, wherein said driving means comprises a rotary solenoid, and said returning means comprises a coiled spring arranged in said rotary solenoid.

* * * * *